United States Patent [19]

Lavagnino et al.

[11] 4,168,388

[45] Sep. 18, 1979

[54] TRIFLUOROMETHYLPHENYL BENZYL ETHERS

[75] Inventors: Edward R. Lavagnino; Bryan B. Molloy; Paul Pranc, all of Indianapolis, Ind.

[73] Assignee: Eli Lilly and Company, Indianapolis, Ind.

[21] Appl. No.: 889,326

[22] Filed: Mar. 23, 1978

[51] Int. Cl.$^2$ ............................................. C07C 43/28
[52] U.S. Cl. ........................... 568/647; 260/340.9 R; 568/585; 568/586; 568/645; 568/775
[58] Field of Search ............ 568/799, 585, 586, 645, 568/647, 775; 260/612 R, 613 R, 340.9 R

[56] References Cited

U.S. PATENT DOCUMENTS

| | | | |
|---|---|---|---|
| 2,159,025 | 5/1939 | Hester | 568/585 |
| 2,213,215 | 9/1940 | Hester | 568/647 X |
| 2,243,479 | 5/1941 | Hester | 568/647 |
| 3,207,786 | 9/1965 | Yale et al. | 568/585 X |

OTHER PUBLICATIONS

Lavagnino et al. OPPI Briefs vol. 9 (1977) pp. 96–98.
Van Duzee et al, JACS, vol. 57 (1935) 147–151.
Hartung et al, Organic Reactions, vol. VII (1963) 268–271, 296–301.
Mooradian et al., J.A.C.S. vol. 73 (1951) 3470–3472.

*Primary Examiner*—Bernard Helfin
*Attorney, Agent, or Firm*—James L. Rowe; Arthur R. Whale

[57] ABSTRACT

Trifluoromethylphenols are prepared by hydrogenation of the corresponding trifluoromethylbenzylethers.

2 Claims, No Drawings

TRIFLUOROMETHYLPHENYL BENZYL ETHERS

BACKGROUND OF THE INVENTION

Many substituted phenols are difficult to synthesize. One common reaction utilizes the replacement of a halogen atom in a substituted chlorobenzene with base. As stated in Billman and Cleland, Methods of Synthesis in Organic Chemistry (Edwards Brothers, Inc., Ann Arbor, Mich. 1954 edition), "[i]t is very difficult to remove a halogen atom from the benzene ring unless there are meta-directing groups in the ortho and/or para positions with respect to the halogen atom." In other words, a misoriented chlorine atom, as in picryl chloride can readily be replaced by hydroxyl using aqueous sodium hydroxide to yield the corresponding phenol, picric acid. Conversion of chlorobenzene, in which there is no misoriented, meta-directing group, to phenol requires the most stringent reaction conditions; for example, reaction temperatures of 300° C., high pressure and flake sodium hydroxide or other alkali. Another method of preparing phenols is by the fusion of an alkali sulfonate or sulfonic acid with sodium hydroxide, also a reaction requiring extreme conditions.

Obviously, reaction conditions which involve extremes of temperature and pressure plus strong alkali are not suitable for the preparation of many substituted phenols and in particular trifluoromethylphenol, since the trifluoromethyl group would be expected to undergo reaction under such extreme conditions.

A second common method of preparing phenols is by the hydrolysis of a substituted phenyldiazonium salt. This synthetic procedure presupposes the preparation of a properly substituted nitrobenzene in which the nitro group is successively reduced to an aniline, the amine group diazotized and the diazonium salt decomposed to yield a phenol. This reaction is not suitable for the preparation of either ortho or para trifluoromethyl phenols since, in the requisite starting material, direct substitution does not produce the desired nitro compound since the trifluoromethyl group is a meta directing group. The trifluoromethyl group can, of course, be prepared from the corresponding carboxylic acid. But again, the carboxylic acid group is a meta directing group and it is difficult to prepare o-or p-nitrobenzoic acids.

Another procedure that has been employed for the preparation of p-trifluoromethylphenol, in particular, has been the chlorination of p-cresol to yield p-trichloromethylphenol. The chlorine atoms can be replaced by fluorine by reaction with antimony pentafluoride. This reaction is a laboratory scale procedure and can not be adapted to commercial production —see R. G. Jones, *J. Am. Chem. Soc.*, 69, 2346 (1947).

Yet another procedure, replacement of the carboxylic acid group in salicylic acid (o-hydroxybenzoic acid) with a trifluoromethyl group by reacting with $SF_4$ plus HF, is also difficult to adapt to a commercial scale because of the problem of handling $SF_4$ although the yields of o-hydroxy compound are reasonable. The reaction, however does not proceed with as good yields where the p-hydroxybenzoic acid is concerned and this acid is, itself, a more difficult to obtain than salicylic acid.

Another approach to the problem of devising synthetic procedures for the preparation of difficultly synthesizable phenols might be termed an indirect approach. In this type of procedure, a given chlorobenzene is nitrated ortho to the chloro group; thus increasing its lability to hydrolytic replacement. Then, the nitro group is removed by the steps of reduction, diazotization of the resulting aniline, and replacement of the azido group by hydrogen. This indirect approach is illustrated by the synthesis of p-trifluoromethylphenol described by Lavagnino et al., *Org. Prep. Proced. Int.* 9, 96 (1977) which was, until the present invention, the best published method for preparing that compound.

It has recently been found by Molloy and Schmiegel that the 3-(trifluoromethylphenoxy)-3-phenylpropylamines, including the primary amines, the secondary N-methyl amines, and the tertiary N,N-dimethylamines are specific inhibitors of the uptake of serotonin, indicating their potential use as psychotrophic drugs in the treatment of depression (see U.S. Pat. No. 4,018,895). These compounds are prepared according to the following general scheme. The keto group of β-diethylaminopropiophenone is reduced to a secondary alcohol with diborane. The hydroxy group is replaced by chlorine using HCl and the chloro compound reacted with the sodium salt of the particular trifluoromethylphenol to yield the desired compound. The corresponding N-methyl compounds are prepared by removal of one of the methyl groups from the N,N-dimethyl derivative using cyanogen bromide. The corresponding primary amines are prepared by a procedure involving the reaction of the desired trifluoromethylphenol sodium salt with 3-chloro-1-bromopropylbenzene. The sodium salt of the phenol reacts preferentially with the bromo group to yield a 3-chloro-1-(trifluoromethylphenoxy)propylbenzene. The chloro compound is then reacted with sodium azide and the resulting azido compound reduced to the primary amine. The same reaction scheme serves to prepare the N-methyl secondary amines by reacting the 3-chloro-1-(trifluoromethylphenoxy)propylbenzene with methylamine instead of $NaN_3$.

Each of the above reaction schemes requires the use of a particular trifluoromethylphenol. It is an object of this invention to provide a new and useful procedure for the preparation of the 3-trifluoromethylphenols, which procedure is well adapted to commercial use. In particular, it is an object of this invention to provide a method for preparing p-trifluoromethylphenol from the relatively cheap intermediate, p-trifluoromethylchlorobenzene. Other objects of this invention will become apparent from the following specification.

SUMMARY OF THE INVENTION

In fulfillment of the above and other objects, this invention provides a method for preparing trifluoromethylphenols comprising the reaction of a trifluoromethylhalobenzene with sodium benzylate or a suitably substituted sodium benzylate. Hydrogenation of the resulting trifluoromethylphenyl benzylether over a heavy metal catalyst serves to remove the benzyl group (as toluene or a substituted toluene) and to provide the desired trifluoromethylphenol in good yield.

The term "halo" in "halobenzene" includes chloro, iodo, bromo and fluoro. We prefer to use, however, either a trifluoromethylchlorobenzene or a trifluoromethylbromobenzene as one reactant in the first step of our novel process.

Although it is preferred to use benzyl alcohol and therefore sodium benzylate in our novel synthetic procedure, chiefly for economic reasons, substituted benzyl alcohols can also be used. The substituent must, of course, be non-reactive to sodium hydride and to the benzylate ion. Among such non-reactive substituents are $C_1$-$C_3$ alkyls such as methyl, nitro, methoxy or methylene dioxy. Useful benzyl alcohols can then be represented by the formula:

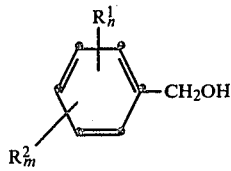

wherein $R^1$ and $R^2$ are individually $C_1$-$C_3$ alkyl, nitro or methoxy, and when taken together and occupying adjacent carbons in the benzene ring, methylene dioxy and n and m are individually 0 or 1. The term $C_1$-$C_3$ alkyl includes methyl, ethyl, n-propyl and isopropyl. Illustrative benzyl alcohols useful for preparing the sodium benzylate reactant thus include o, m and p-nitrobenzyl alcohol
o, m and p-methoxybenzyl alcohol
o, m and p-methylbenzyl alcohol
3,4-methylenedioxybenzyl alcohols
3,5-dinitrobenzyl alcohol
p-isopropylbenzyl alcohol (cumic alcohol)
o, m and p-ethylbenzyl alcohol
2-methyl-4-methoxybenzyl alcohol
2,3-, 2,4- and 3,4-dimethoxybenzyl alcohol In choosing a suitable benzyl alcohol for use in our novel process, two separate and opposing aspects of the chemistry of the two steps should be considered.

On the one hand, with one or more electron-withdrawing substituents ortho or para to the benzyl group, the formation of the sodium salt and the reactivity of the benzylate ion is enhanced. The opposite would of course be true with an electron-donating substituent. On the other hand, the presence of an electron-withdrawing substituent decreases the reactivity of the benzylate ion vis-a-vis the hydrogenation reaction, since an electron-withdrawing group would tend to strengthen the carbon-oxygen bond. An electron-donating group would have an opposite effect. An o or p-nitrobenzyl alcohol has the interesting characteristic of bearing an electronegative substituent, which promotes benzylate ion and benzyl ether ion formation. However, upon hydrogenation, the nitro group is first reduced to the electron-donating amino group which tends to ease hydrogenolysis of the phenyl benzyl ether.

While the above considerations are real, reaction conditions can readily be adjusted to compensate for relative lack of reactivity. Hence for most purposes, economic considerations are the most important and the abundant and inexpensive reagent, benzyl alcohol, is preferred.

DETAILED EXEMPLIFICATION OF THE INVENTION

Reaction Scheme I illustrates the invention. In the Reaction Scheme, the synthesis of p-trifluoromethylphenol is used for exemplary purposes only, and it should be understood that the synthesis applies equally well to the preparation of m-trifluoromethylphenol and o-trifluoromethylphenol. Benzyl alcohol is also used for exemplary purposes only.

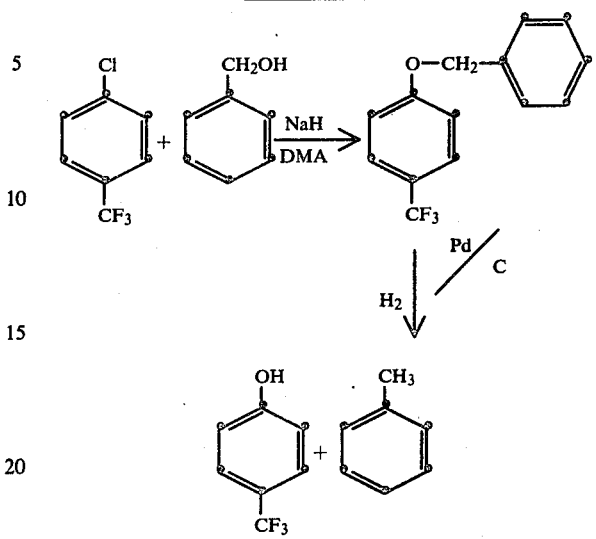

Reaction Scheme I

According to the above reaction scheme, the sodium salt of benzyl alcohol is prepared using, for example, sodium hydride, sodium amide and the like and a suitable non-reactive solvent such as N,N-dimethylacetamide (DMA) diglyme, DMF or the like. After the reaction between sodium hydride and benzyl alcohol has gone substantially to completion to form sodium benzylate, a solution of trifluoromethylchlorobenzene in the same solvent is added, and the consequent reaction mixture heated until the reaction forming the ether has gone substantially to completion, usually requiring from one to two days. The reaction is carried out under a nitrogen atmosphere. The trifluoromethylphenyl benzyl ether product of the reaction is isolated by diluting the reaction mixture with water. If the ether crystallizes, it can be separated by filtration. Non-crystalline ethers are isolated by extracting the aqueous phase with a water-immiscible solvent, separating the organic layer, removing the solvent in vacuo and distilling the ether residue. The second step of the reaction, the hydrogenolysis of the ether, employs a heavy metal catalyst such as 5 percent palladium-on-carbon, platinum oxide, palladium-on-calcium sulfate, or the like. The hydrogenation is carried out in a sealed container at a relatively low pressure, 50-100 psi of hydrogen. The trifluoromethylphenol is isolated by first removing the catalyst by filtration and then concentrating the filtrate. The phenol is readily purified by distillation. A suitable solvent for the hydrogenation step is a lower alcohol such as ethanol.

This invention is further illustrated by the following specific examples:

EXAMPLE 1

Preparation of 4-Trifluoromethylphenyl Benzyl Ether 110 gms. of sodium hydride as a 50 percent oil dispersion were washed with hexane under a nitrogen atmosphere (to remove the oil). 500 ml. of DMA were then added followed by 251 g., in small portions, of benzyl alcohol in 1 liter of DMA. The reaction was exothermic. After the addition had been completed, the mixture was stirred for one hour at 80°-90° C. thus insuring completion of the formation of sodium benzylate. Next, 420 g. of 4-trifluoromethylchlorobenzene in 1 liter of DMA were added. The reaction mixture was refluxed under a nitrogen atmosphere for about 18 hours and was then cooled. Two liters of water were added to the cooled solution. 4-Trifluoromethylphenyl benzyl ether formed in the above reaction crystallized on cooling and was collected by filtration. Recrystallization from methanol yielded 390 g. of the ether (66.5 percent yield) melting at 77°–79° C.

Analysis Calc.: C, 66.67; H, 4.40 Found: C, 66.57; H, 4.27

Following the above procedure, but substituting 2-trifluoromethylchlorobenzene for 4-trifluoromethylchlorobenzene, 2-trifluoromethylphenyl benzyl ether was prepared in 68 percent yield. The ether boiled 127°–128° C. at 5 torr.

Analysis Calc.: C, 66.67; H, 4.40 Found: C, 66.77; H, 4.45

Following the above procedure, but substituting 3-trifluoromethylchlorobenzene for 4-trifluoromethylchlorobenzene, 3-trifluoromethylphenyl benzyl ether was prepared in 68 percent yield. The ether boiled in the range 112°–116° C. at 5 torr. The distilled product solidified and melted at 56°–58° C.

Analysis Calc.: C, 66.67; H, 4.40 Found: C, 66.75; H, 4.62

EXAMPLE 2

Preparation of 4-Trifluoromethylphenol

A solution of 390 g. of 4-trifluoromethylphenyl benzyl ether in 3580 ml. of ethanol was placed in a low pressure hydrogenation vessel along with 30 g. of 5 percent palladium-on-carbon. An initial hydrogen pressure of 60 psi was used and the solution was hydrogenated at room temperature until the theoretical uptake of hydrogen had been achieved—about 2 hours. The catalyst was removed by filtration. Concentration of the filtrate yielded 4-trifluoromethylphenol, distilling in the range 51°–54° C. at 6 torr. Yield=212 gms. (84.5 percent).

Following the above procedure, but hydrogenating 2-trifluoromethylphenylbenzyl ether, there was obtained a 75% yield of 2-trifluoromethylphenol boiling in the range 147°–8° C. at 1 atmo.

Following the above procedure, but hydrogenating 3-trifluoromethylphenyl benzyl ether, there was prepared 3-trifluoromethylphenol in 79 percent yield boiling in the range 57°–60° C. at 9 torr.

The process of this invention is particularly well suited for the commerical production of 4-trifluoromethylphenol. The starting material, 4-trifluoromethylchlorobenzene, is prepared by the fluorination of 4-chlorobenzoic acid and is readily available from many commercial sources as are the other 4-trifluoromethylhalo benzenes. Chlorobenzoic acid itself is made by the oxidation of 4-chlorotoluene which comproxund can in turn be readily prepared by the chlorination of toluene followed by an isomer separation step.

Alternate methods of preparation of 4-trifluoromethylphenol are not very attractive commercially. For example, attempts to replace the chlorine in 4-trifluoromethylchlorobenzene with hydroxide in the presence of base would undoubtedly result in the hydrolysis of the trifluoromethyl group. The diazotization route is also not attractive. In the first place, trifluoromethylbenzene, can not be nitrated in the para position since the trifluoromethyl group is a deactivating or meta-directing group. Likewise, benzoic acid cannot be nitrated in the para position for the same reasons. Thus, toluene itself would have to be nitrated and the isomers separated. The procedure from thereon would involve oxidation of the methyl group in toluene, reduction of the nitro group, diazotization of the amine group, replacement of the diazo group by hydroxyl and finally fluorination of the carboxylic acid group. This route is obviously far more cumbersome and costly than the synthetic route of this invention.

We claim:

1. As a new composition of matter, a compound of the formula

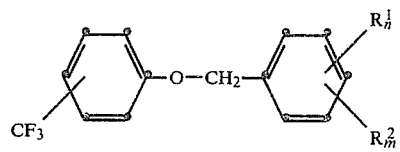

wherein $R^1$ and $R^2$ when taken individually are nitro, $C_1$–$C_3$ alkyl or methoxy and when taken together and when occupying adjacent carbons, methylenedioxy and n and m taken individually are 0 and 1.

2. A compound according to claim 1, said compound being 4-trifluoromethylphenyl benzyl ether.

* * * * *

Disclaimer 4,168,388.—*Edward R. Lavagnino; Bryan B. Molloy* and *Paul Pranc,* Indianapolis, Ind. TRIFLUOROMETHYLPHENYL BENZYL ETHERS. Patent dated Sept. 18, 1979. Disclaimer filed Nov. 16, 1981, by the assignee, *Eli Lilly and Co.*

Hereby enters this disclaimer to all of the claims of said patent.

[*Official Gazette January 26, 1982.*]